US010667779B2

(12) United States Patent
Tobita et al.

(10) Patent No.: US 10,667,779 B2
(45) Date of Patent: Jun. 2, 2020

(54) OPERATION DEVICE AND X-RAY IMAGING UNIT (71) Applicant: OMRON CORPORATION, Kyoto-shi, Kyoto (JP)

(72) Inventors: Kokichi Tobita, Unnan (JP); Koichi Furusawa, Okayama (JP); Makoto Wada, Okayama (JP)

(73) Assignee: OMRON Corporation, Kyoto-shi (JP)

(*) Notice: Subject to any disclaimer, the term of this patent is extended or adjusted under 35 U.S.C. 154(b) by 152 days.

(21) Appl. No.: 15/575,409

(22) PCT Filed: Jul. 25, 2016

(86) PCT No.: PCT/JP2016/071775
§ 371 (c)(1),
(2) Date: Nov. 20, 2017

(87) PCT Pub. No.: WO2017/022551
PCT Pub. Date: Feb. 9, 2017

(65) Prior Publication Data
US 2018/0153499 A1 Jun. 7, 2018

(30) Foreign Application Priority Data

Aug. 6, 2015 (JP) ................................. 2015-156476

(51) Int. Cl.
A61B 6/00 (2006.01)
G08C 17/00 (2006.01)
(Continued)

(52) U.S. Cl.
CPC .............. A61B 6/548 (2013.01); A61B 6/586 (2013.01); G08C 17/00 (2013.01); H01H 3/12 (2013.01);
(Continued)

(58) Field of Classification Search
None
See application file for complete search history.

(56) References Cited

U.S. PATENT DOCUMENTS 5,206,894 A * 4/1993 Makrinos ............... A61B 6/467
378/114
6,111,518 A 8/2000 Han
(Continued)

FOREIGN PATENT DOCUMENTS

CN 202395925 U 8/2012
CN 103747313 A 4/2014
(Continued)

OTHER PUBLICATIONS

The Australian Office Action dated Apr. 5, 2019 in a counterpart Australian patent application.
(Continued)

Primary Examiner — Hoon K Song
(74) Attorney, Agent, or Firm — Metrolex IP Law Group, PLLC (57) ABSTRACT An operation device (200) for remotely operating an X-ray imaging device (1) includes an operation unit (280), a grip detection unit (240), which determines whether an operation received by the operation unit (280) is a normal operation or an erroneous operation, and a control unit (230), which transmits an operation signal corresponding to the operation to the X-ray imaging device (1). The control unit (230) transmits the signal when the grip detection unit (240) determines that the operation is a normal operation. The operation device is prevented from causing an erroneous operation of its target device.

6 Claims, 8 Drawing Sheets (51) Int. Cl.
- *H01H 13/50* (2006.01)
- *H04Q 9/00* (2006.01)
- *H01H 3/12* (2006.01)
- *H01H 13/64* (2006.01)
- *H01H 9/02* (2006.01)

(52) U.S. Cl.
CPC ............ *H01H 13/503* (2013.01); *H04Q 9/00* (2013.01); *A61B 6/4405* (2013.01); *A61B 6/467* (2013.01); *A61B 6/56* (2013.01); *H01H 9/0214* (2013.01); *H01H 13/64* (2013.01)

(56) References Cited

U.S. PATENT DOCUMENTS

| | | | |
|---|---|---|---|
| 6,144,756 A * | 11/2000 | Takahashi | G06K 9/0002 382/124 |
| 2007/0054651 A1 | 3/2007 | Farmer et al. | |
| 2009/0051481 A1 | 2/2009 | Park et al. | |
| 2009/0080348 A1 | 3/2009 | Hamel et al. | |
| 2009/0248223 A1 | 10/2009 | Ecton et al. | |
| 2012/0100917 A1 | 4/2012 | Yung | |
| 2012/0139698 A1 | 6/2012 | Tsui et al. | |
| 2012/0144848 A1 | 6/2012 | Yeo et al. | |
| 2012/0274218 A1 * | 11/2012 | Mountain | H04M 1/22 315/152 |

FOREIGN PATENT DOCUMENTS

| | | |
|---|---|---|
| EP | 1073027 A1 | 1/2001 |
| JP | H01-270486 A | 10/1989 |
| JP | H02-201523 A | 8/1990 |
| JP | 2000270236 A | 9/2000 |
| JP | 2007-325856 A | 12/2007 |
| JP | 2007-329815 A | 12/2007 |
| JP | 2010-109960 A | 5/2010 |
| JP | 2010-284363 A | 12/2010 |
| KR | 20100047765 A | 5/2010 |
| WO | 0060534 A1 | 10/2000 |
| WO | 2014/119812 A1 | 8/2014 |

OTHER PUBLICATIONS

English translation of Written Opinion of PCT/JP2016/071775 dated Feb. 15, 2018 from the International Searching Authority.
The (translated) International Search Report of PCT/JP2016/071775 dated Oct. 18, 2016.

* cited by examiner

OPERATION DEVICE AND X-RAY IMAGING UNIT

FIELD

The present invention relates to an operation device for remotely operating a target device, and an X-ray imaging unit including the operation device.

BACKGROUND

X-ray imaging devices for capturing X-ray images are known. A common X-ray imaging device now includes a wired controller. The controller is operated to capture X-ray images.

However, a wired controller limits the range in which the operator can move. Also, the controller can have a cable that is as long as about 10 meters. The weight of the cable can lower the operability of the controller. Further, the cable may become dirty after use and is to be replaced regularly.

In response to this issue, a wireless controller for an X-ray imaging device is described in Patent Literature 1.

A remote controller including conductive side rails is described in Patent Literature 2. The remote controller described in Patent Literature 2 reduces power consumption using a power saving mode entered when no object is in contact with the side rails.

CITATION LIST

Patent Literature

Patent Literature 1: U.S. Pat. No. 5,206,894
Patent Literature 2: U.S. Patent Application Publication No. 2007/0054651A1

SUMMARY

Technical Problem

While not capturing X-ray images, the operator of an X-ray imaging device with a wireless controller is involved in other tasks, with the controller placed in, for example, a pocket of his or her clothing. Also, the operator of an X-ray imaging device with a wired controller may also be involved in other tasks with the controller placed in, for example, a pocket of his or her clothing. The controller placed in the pocket may be operated accidentally. Any such erroneous operation of the controller for the X-ray imaging device can cause unintended exposure of the operator to X-rays.

In response to the above issue, one or more aspects of the present invention are directed to an operation device that is prevented from causing an erroneous operation in remotely operating a target device, such as an X-ray imaging device.

Solution to Problem

The operation device according to the above aspects of the present invention is used to remotely operate a target device. The operation device includes an operation unit that receives an operation from an operator, a determination unit that determines whether the operation received by the operation unit is a normal operation or an erroneous operation, and a control unit that transmits an operation signal corresponding to the operation received by the operation unit to the target device when the determination unit determines that the operation is a normal operation.

Advantageous Effects

The operation device and the X-ray imaging unit including the operation device according to the above aspects are prevented from causing an erroneous operation in remotely operating a target device, such as an X-ray imaging device.

DETAILED DESCRIPTION

Embodiments of the present invention will now be described in detail with reference to the drawings.

First Embodiment

Figure 1:
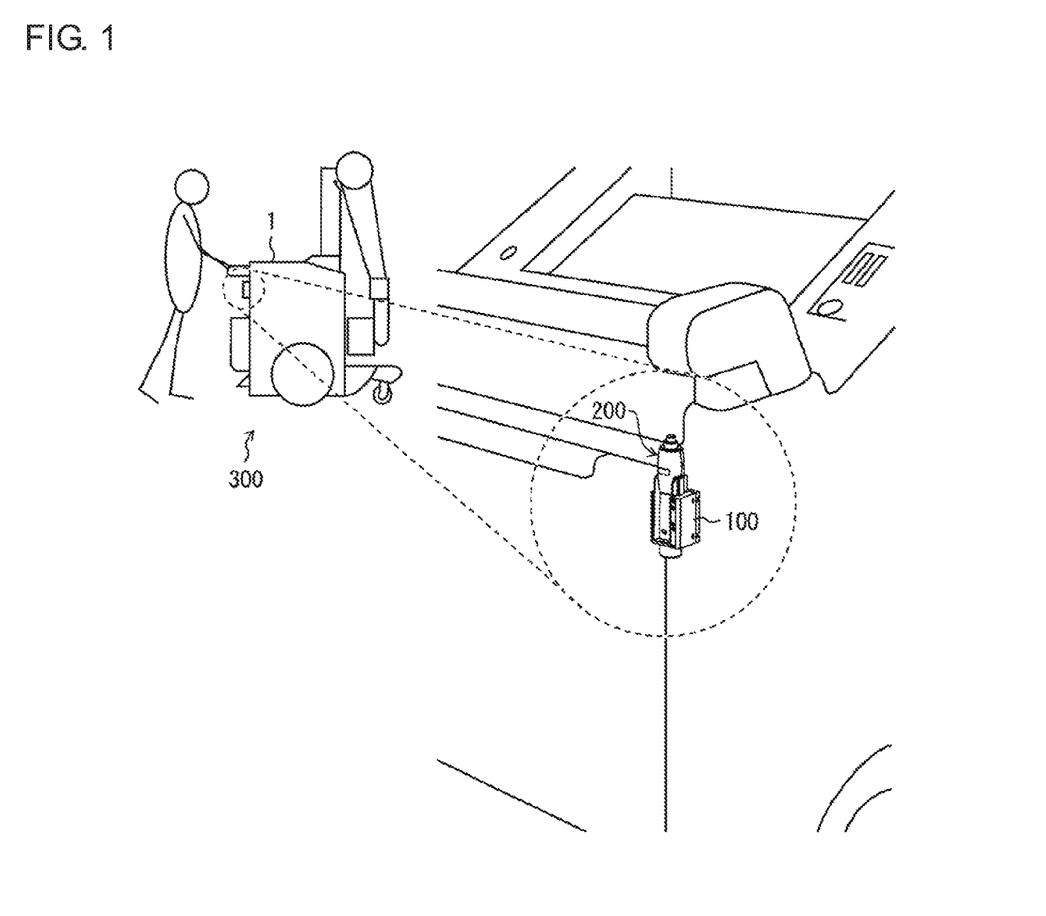
FIG. 1 is an external view of an X-ray imaging unit including an operation device according to one embodiment of the present invention.

FIG. 1 is a perspective view of an operation device for operating a target device according to the present embodiment, together with a holder and the target device. The target device is an X-ray imaging device 1, which irradiates a patient with X-rays and detects the X-rays transmitted through the patient to generate X-ray images. As shown in FIG. 1, the X-ray imaging device 1 includes a holder 100, which holds an operation device 200 in a removable manner.

Figure 2:
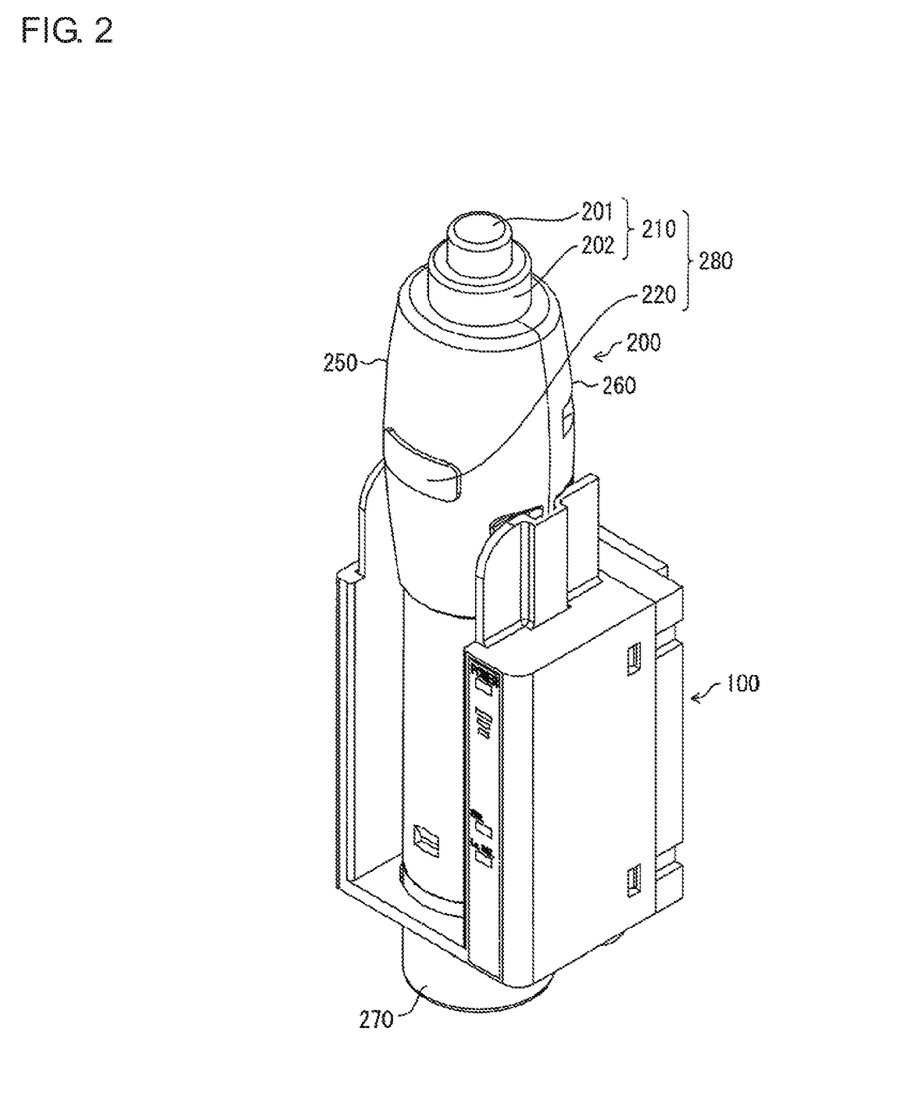
FIG. 2 is an external perspective view of the operation device and the holder included in the X-ray imaging unit shown in FIG. 1.

FIG. 2 is a diagram showing the operation device according to the present embodiment. The operation device 200 is a remote controller for remotely operating the X-ray imaging device 1. The operation device 200 includes a front case 250, a rear case 260, and a bottom cap 270, which hold the parts of the operation device 200. The operation device 200 is substantially cylindrical. The operation device 200 includes a main switch 210 on its upper surface and an optional switch 220 in an upper portion of its peripheral surface to allow the user gripping the peripheral surface of the operation device 200 to operate the main switch 210 with a thumb and the optional switch 220 with a forefinger.

The main switch 210, which operates in two stages, includes first and second switch members 201 and 202 set at different home positions when not pressed by the user. The first switch member 201 has a longer stroke distance from its home position than the second switch member 202.

An operation unit 280 includes the main switch 210 and the optional switch 220 for receiving operations performed by the operator. The main switch 210 is pressed to output an instruction for X-ray imaging to the X-ray imaging device 1, and the optional switch 220 is pressed to output, to the X-ray imaging device 1, an instruction for turning on or off a lighting instrument included in the X-ray imaging device 1 for indicating the range of X-ray irradiation performed by the X-ray imaging device 1.

Figure 3A:
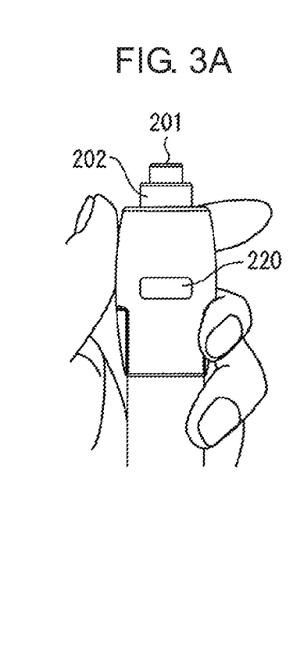
FIGS. 3A to 3D are diagrams showing the operation device being operated by an operator.
Figure 3B:
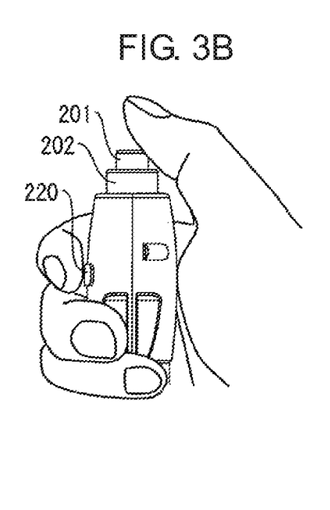
Figure 3C:
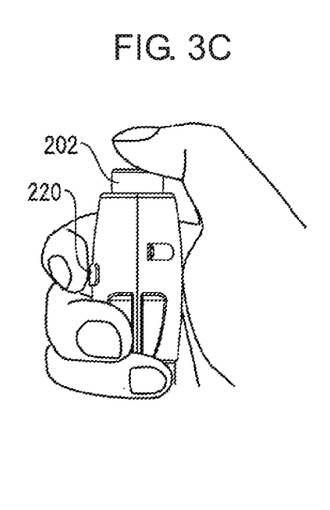
Figure 3D:
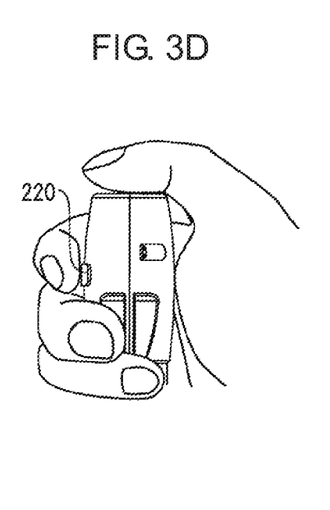

The main switch 210 includes the first and second switch members 201 and 202. When the user presses the first switch member 201 to the home position of the second switch member 202, the operation device 200 outputs an instruction for charging an X-ray imaging circuit (through the holder 100) to the X-ray imaging device 1 (refer to FIGS. 3A to 3C). When the first switch member 201 remains in the pressed state for a predetermined time, the X-ray imaging circuit is fully charged and becomes ready for imaging. When both the first switch members 201 and the second switch member 202 are pressed to the full-stroke position, the operation device 200 outputs an instruction for X-ray imaging (through the holder 100) to the X-ray imaging device 1 (refer to FIG. 3D).

Figure 4:
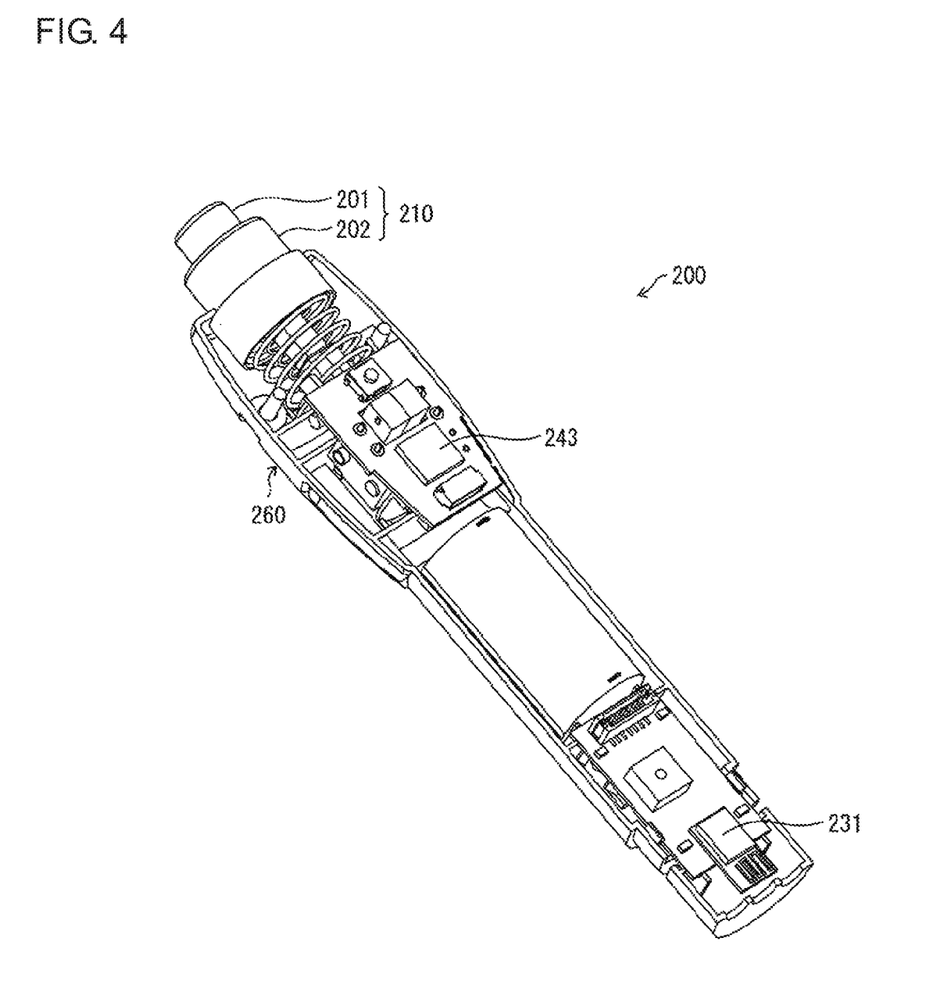
FIG. 4 is a diagram showing the operation device shown in FIG. 2 with its front case and its bottom cap being removed.
Figure 5:
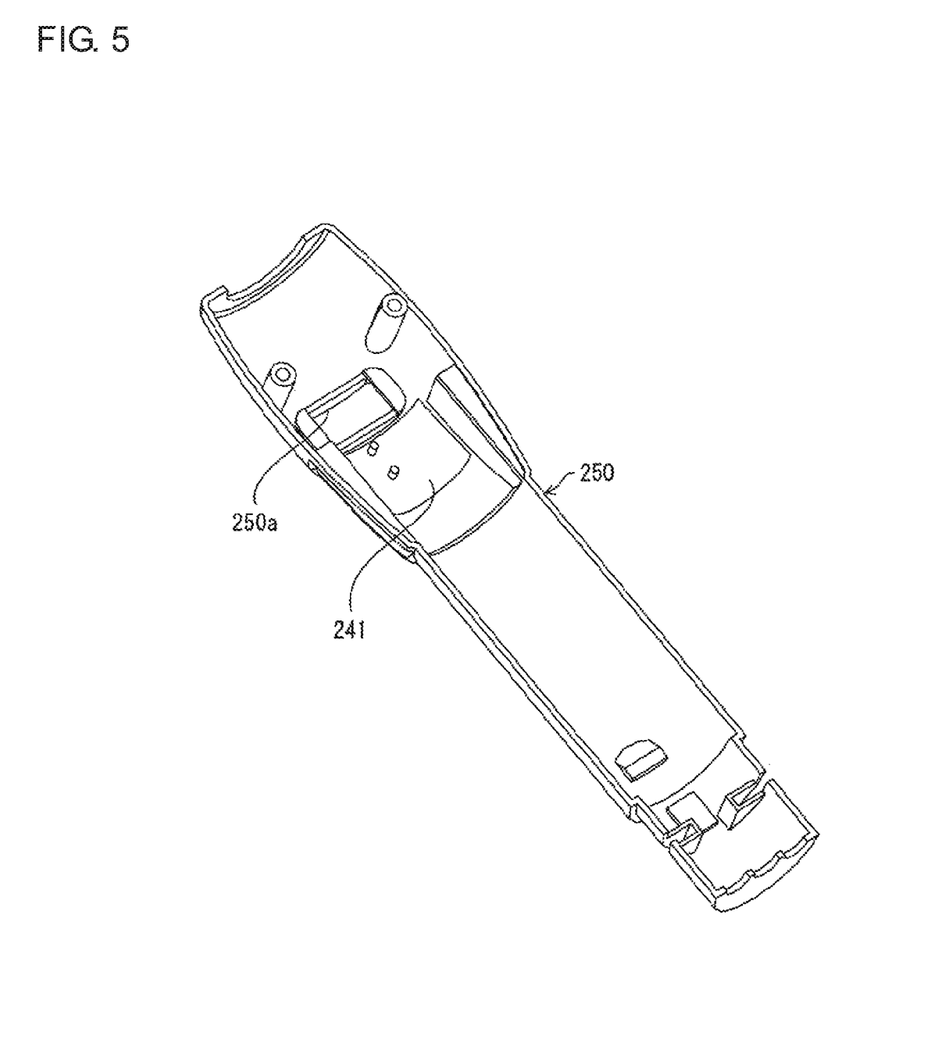
FIG. 5 is a diagram showing the front case and a front electrode for the operation device shown in FIG. 2.
Figure 6:
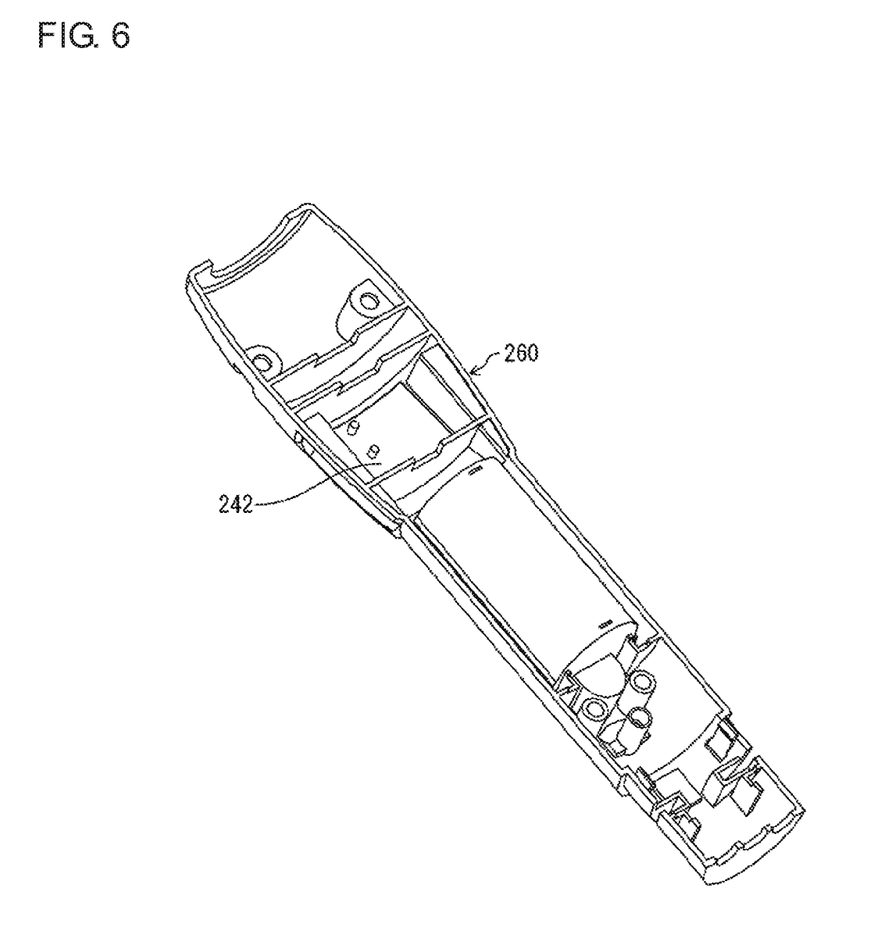
FIG. 6 is a diagram showing a rear case and a rear electrode for the operation device shown in FIG. 2.

FIGS. 4 to 6 are diagrams each showing the internal structure of the operation device 200. FIG. 4 is a diagram showing the operation device 200 with the front case 250 and the bottom cap 270 being removed. FIG. 5 is a diagram showing the front case 250 and a front electrode 241. FIG. 6 is a diagram showing the rear case 260 and a rear electrode 242.

As shown in FIGS. 4 to 6, the operation device 200 includes a touch sensor IC 243, the front electrode 241, the rear electrode 242, and a communication unit 231.

The front electrode (sensor) 241 and the rear electrode (sensor) 242 are electrodes for capacitance touch sensors. The front case 250 has a hole 250a, at a position where the optional switch 220 is to be installed. The front electrode 241 is arranged adjacent to the hole 250a (in a direction opposite to the installation position of the main switch 210) to extend along the inner wall of the front case 250. The rear electrode 242 is arranged along the inner wall of the rear case 260 at a position to radially face the front electrode 241.

The touch sensor IC 243 is electrically connected to the front electrode 241 and the rear electrode 242 to detect whether the operation device 200 is gripped by the operator based on a change in the capacitance of each of the front electrode 241 and the rear electrode 242. The detection method will be described in detail later.

The communication unit 231 wirelessly transmits an operation signal that is generated based on an operation of the operation unit 280 to the holder 100. The communication unit 231 may use any wireless communication protocol, such as Bluetooth (registered trademark) or communication using infrared rays.

Figure 7:
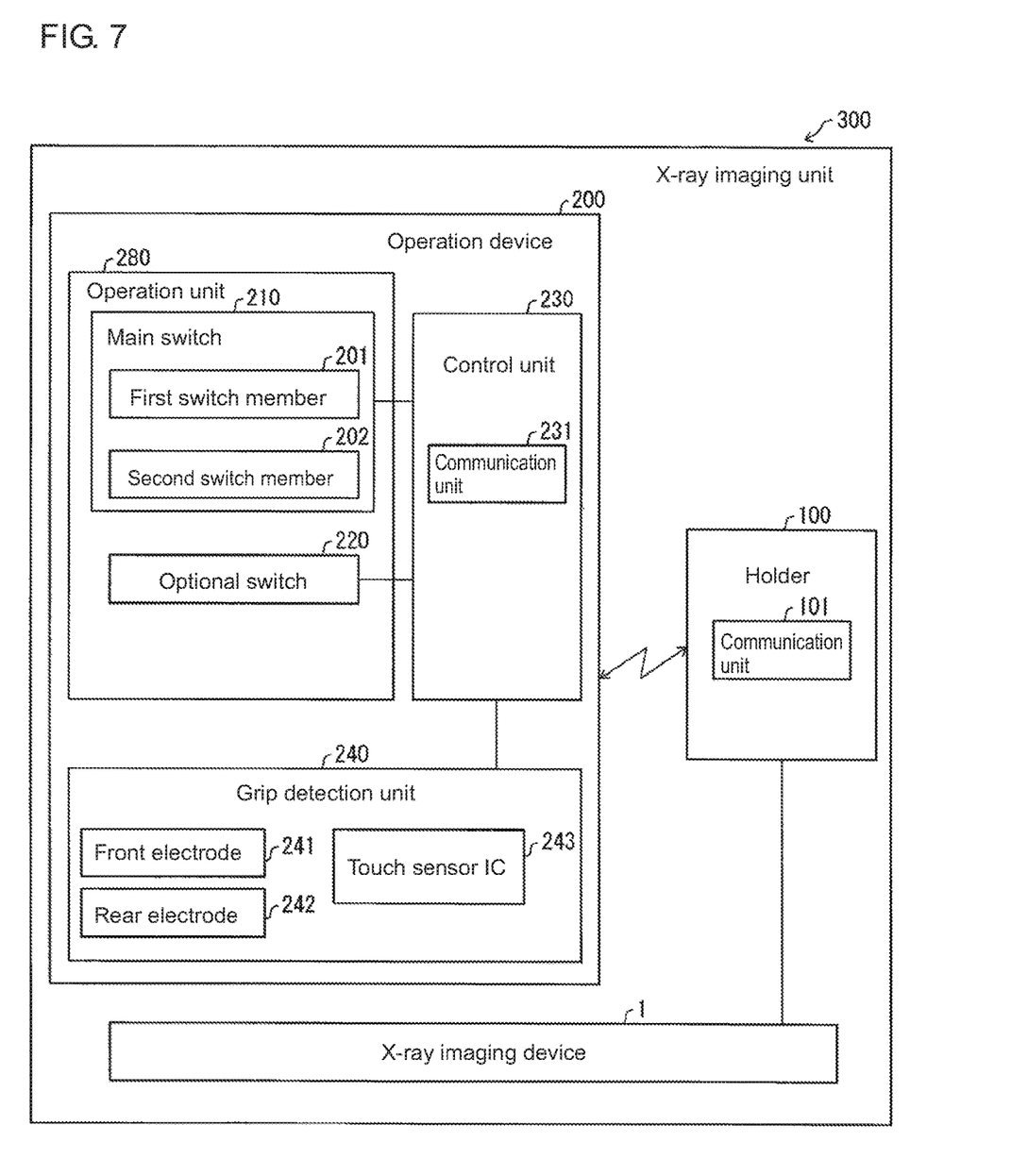
FIG. 7 is a block diagram of the X-ray imaging unit 300 shown in FIG. 1.

FIG. 7 is a block diagram of the X-ray imaging unit 300 including the operation device 200 according to the present embodiment. As shown in FIG. 7, the X-ray imaging unit 300 includes the X-ray imaging device 1, the holder 100, and the operation device 200.

The holder 100 wirelessly communicates with the operation device 200. The holder 100 receives an operation signal transmitted from the operation device 200 through the communication unit 101, and transmits the operation signal to the X-ray imaging device 1.

The operation device 200 includes the operation unit 280, a control unit 230, and a grip detection unit (determination unit) 240.

The grip detection unit 240 includes the front electrode 241, the rear electrode 242, and the touch sensor IC 243. The grip detection unit 240 detects whether the operator is gripping the operation device 200, or the operation device 200 is in a gripped state based on a change in the capacitance of each of the front electrode 241 and the rear electrode 242, and generates grip information indicating whether the operation device 200 is in the gripped state. In other words, the grip detection unit 240 serves as a determination unit that determines whether an operation received by the operation unit 280 is a normal operation intended by the operator or an erroneous operation that is unintended by the operator.

More specifically, when the operator grips the operation device 200 to operate the operation unit 280, the operator's fingers touch a part of the front case 250 containing the front electrode 241 and a part of the rear case 260 containing the rear electrode 242. This produces a change in the capacitance of each of the front electrode 241 and the rear electrode 242. When the capacitance in both the front electrode 241 and the rear electrode 242 changes, the touch sensor IC 243 determines that the operation device 200 is in the gripped state.

As described above, the operation unit 280 includes the main switch 210, which includes the first switch member 201 and the second switch member 202, and the optional switch 220. When the operator operates the main switch 210 and the optional switch 220, the operation unit 280 transmits, to the control unit 230, an operation signal corresponding to the operation.

When receiving the operation signal from the operation unit 280, the control unit 230 obtains grip information from the grip detection unit 240. When the obtained grip information indicates that the operation device 200 is in the gripped state, the control unit 230 transmits the operation signal to the holder 100 through the communication unit 231. When the obtained grip information indicates that the operation device 200 is not in the gripped state, the control unit 230 does not transmit the operation signal to the holder 100.

In one example, the operator removes the operation device 200 from the holder 100 and places the operation device 200 into a pocket of his or her clothing, and is involved in tasks other than X-ray imaging. The operation device 200 placed in the pocket may then be accidentally operated. In this case, one of the front electrode 241 and the rear electrode 242 in the pocket can sense the operator through his or her clothing to change its capacitance, whereas the other electrode does not sense the operator. In this case, the touch sensor IC 243 determines that the operation device 200 is not in the gripped state. The erroneous operation of the operation unit 280 does not cause an operation signal to be transmitted, and thus does not cause the X-ray imaging device 1 to emit X-rays.

The tasks other than X-ray imaging may include assisting a patient, during which the operation device 200 placed in the pocket may touch a bed or other objects. However, the grip detection unit 240 determines that the operation device 200 is in the gripped state only when both the part containing the front electrode 241 and the part containing the rear electrode 242 come in contact with conductors. One of the front electrode 241 and the rear electrode 242 touching the operator through his or her clothing and the other electrode touching a non-conductor such as a bed do not cause the grip detection unit 240 to determine that the operation device 200 is in the gripped state.

As described above, the operation device 200 according to the present embodiment includes the two electrodes that serve as sensors for detecting a human body touch, and detects the gripped state only when both the two electrodes detect touches. When the operation unit 280 is operated unintentionally without the operation device 200 being gripped by the operator, no operation signal is transmitted to the X-ray imaging device 1. This structure prevents an erroneous operation, or an operation unintended by the operator, from causing the X-ray imaging device 1 to emit X-rays.

Modifications

In the above embodiment, although the operation device 200 includes two electrodes as touch sensor electrodes, or specifically the front electrode 241 and the rear electrode 242, the operation device 200 may include any number of such electrodes that are at least two electrodes. For example, the operation device 200 may include three or four electrodes. For the operation device 200 including three or more touch sensor electrodes, the touch sensor IC 243 included in the grip detection unit 240 detects the gripped state when two or more of the electrodes detect a touch of a human body on the operation device 200. In other words, the grip detection unit 240 detects the gripped state when detecting a human touch in two different directions. The touch sensor electrodes may be arranged at any position that allows detection of a human body touch on a gripping part of the operation device 200 that is gripped by the operator.

Although the grip detection unit 240 detects whether the operation device 200 is in the gripped state of being gripped by the operator using the capacitance touch sensors in the above embodiment, the grip detection unit 240 may use other components to detect the gripped state. For example, the grip detection unit 240 may use pressure-sensitive sensors or mechanical switches as the sensors to detect the gripped state.

In the above embodiment, the operation device 200 wirelessly communicates with the holder 100 and transmits an operation signal to the X-ray imaging device 1 through the holder 100. In some embodiments, the X-ray imaging device 1 may include a communication unit, and the operation device 200 may wirelessly communicate with the communication unit and transmit an operation signal to the X-ray imaging device 1.

In the above embodiment, the control unit 230 obtains grip information from the grip detection unit 240 in response to an operation signal received from the operation unit 280 and determines whether the operation signal is to be transmitted based on the obtained grip state information. In some embodiments, the control unit 230 may obtain grip information from the grip detection unit 240 in response to an operation signal received from the operation unit 280 and may then associate the operation signal with the grip information and transmit the resultant information to the holder 100 as operation information. In this case, the holder 100 or the X-ray imaging device 1 may refer to the grip information included in the operation information and determine whether an operation corresponding to the operating signal associated with the grip information is to be performed based on the grip information.

Although the operation device 200 wirelessly communicates with the holder 100 in the above embodiment, the operation device 200 may be connected to the X-ray imaging device 1 with a cable to remotely operate the X-ray imaging device 1. The operation device 200 connected to the X-ray imaging device 1 with a cable may also be placed in the operator's pocket while the operator is involved in other tasks. The grip detection unit 240 prevents an erroneous operation in this case.

Although the operation device 200 includes the grip detection unit 240 as the determination unit that determines whether the operation received by the operation unit 280 is a normal operation intended by the operator or an erroneous operation unintended by the operator in the above embodiment, the determination may be performed by a unit other than the grip detection unit 240.

For example, the operation device 200 may include an acceleration sensor, and an inclination detection unit that serves as the determination unit. In this modification, the inclination detection unit detects an inclination of the operation device 200 based on an output value from the acceleration sensor, and determines whether the operation is a normal operation or an erroneous operation based on the inclination. More specifically, the inclination detection unit may determine that the operation is a normal operation when the angle of inclination of the operation device 200 detected based on an output value from the acceleration sensor falls within a predetermined range or within a range allowed for the operator to operate the operation device 200. The inclination detection unit may determine that the operation is an erroneous operation when the angle of inclination is outside the predetermined range. The operation on the operation unit 280 performed by the operator is determined to be a normal operation when the angle of inclination of the operation device 200 is within the predetermined range. When the operation device 200 is placed in a pocket, the angle of inclination of the operation device 200 falls outside the predetermined range. In this case, the inclination detection unit determines any operation on the operation unit 280 to be an erroneous operation. The operation signal is not transmitted, and the operation device 200 is thus prevented from causing an erroneous operation of its target device.

The operation device 200 may include a plurality of luminance sensors and a luminance detection unit that serves as the determination unit. The luminance detection unit uses output values from the luminance sensors and determines whether an operation is a normal operation or an erroneous operation. More specifically, the luminance sensors are arranged at positions other than the gripping part of the operation device 200 to be gripped by the operator. For example, the operation device 200 includes the luminance sensors arranged in its top and bottom ends of the operation device 200 in the longitudinal direction, at which light is not blocked by the operator's hand gripping the operation device 200. When both the luminance sensors are detecting light, the luminance detection unit determines that the operation is a normal operation. When the operator grips the operating device 200 to operate the operation unit 280, both the two luminance sensors detect light, and the luminance detection unit determines that this operation is a normal operation. When the operation device 200 is entirely placed in a pocket, the luminance sensors detect no light. When a half of the operation device 200 is placed in a pocket, one of the luminance sensors detects light and the other luminance sensor detects no light. The luminance detection unit determines that the operation is a normal operation only when both the luminance sensors detect light. This structure prevents the operation device 200 from causing an erroneous operation of its target device.

Second Embodiment

Another embodiment of the present invention will now be described with reference to FIG. 8. For ease of explanation, the components having the same functions as the components described in the above embodiments are given the same reference numerals as those components, and will not be described.

Figure 8A:
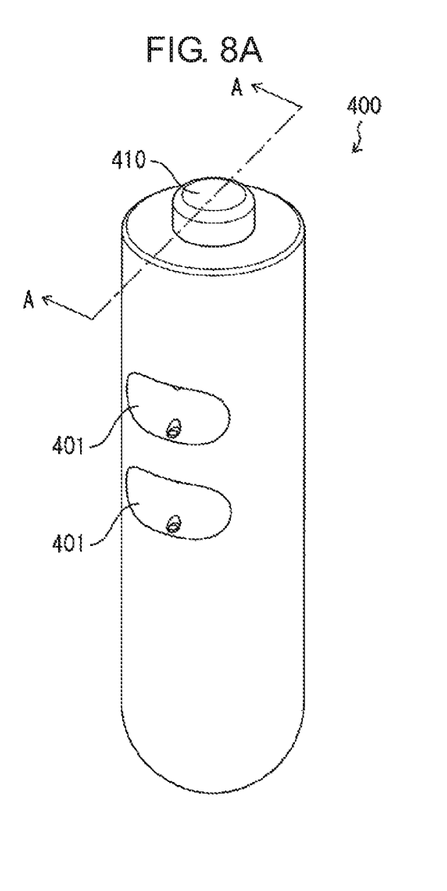
FIG. 8A is an external perspective view of an operation device 400 according to a second embodiment.
Figure 8B:
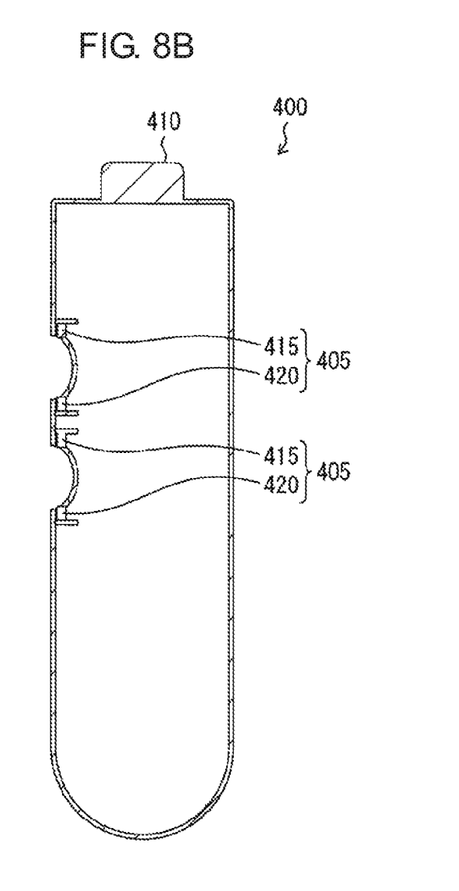
FIG. 8B is a schematic cross-sectional view taken along line A-A in FIG. 8A.

FIG. 8A is an external perspective view of an operation device 400 according to the second embodiment. FIG. 8B is a schematic cross-sectional view taken along line A-A in FIG. 8A.

The operation device 400 is substantially cylindrical. The operation device 400 includes a main switch 410 on its upper surface, two recesses 401 on its peripheral surface, and sensors 405 mounted in the two recesses 401.

The main switch 410 is a push-button switch that receives a press operation performed by an operator.

The recesses 401 on the peripheral surface of the operation device 400 are at positions where any finger(s) of the operator can be placed to grip the operation device 400 with one hand when the operator intends to operate the main switch 410. Each recess 401 is shaped in accordance with the size of a finger.

The sensors 405 each include a light emitter 415 and a light receiver 420. The light emitter 415 and the light receiver 420 of each sensor 405 face each other in the recess 401 in the longitudinal direction of the operation device 400. In the sensor 405, light emitted from the light emitter 415 is received by the light receiver 420 to detect an object present between the light emitter 415 and the light receiver 420. When the operator grips the operation device 400, his or her fingers can be placed in the recesses 401. The sensors 405 then detect that the operation device 400 is gripped.

The operation device 400 according to the second embodiment includes a grip detection unit (determination unit) 240, in the same manner as the operation device 200 according to the first embodiment. The grip detection unit 240 is connected to the sensors 405. When at least one of the two sensors 405 detects an object, the grip detection unit 240 detects that the operation device 400 is in a gripped state. Although an operation of the main switch 410 is caused by an unintended movement of the operator due to, for example, the operation device 400 placed in a pocket being in contact with a bed, the operation does not cause the operation signal to be transmitted to the X-ray imaging device 1 unless the sensors 405 detect an object. Additionally, the sensors 405 arranged in the recesses 401 do not detect an object when the operation device 400 is in contact with a flat surface.

The recesses 401 are each sized in accordance with the size of a finger. The recesses 401 each cannot receive an object larger than a finger. This structure prevents the grip detection unit 240 from erroneously detecting the gripped state based on a touch of an object larger than a finger.

Although the grip detection unit 240 detects the gripped state when at least one of the two sensors 405 detects an object in the present embodiment, the grip detection unit 240 may detect the gripped state when both the two sensors 405 detect an object. This modification prevents an operation signal for an erroneous operation from being transmitted to the X-ray imaging device 1 in a more reliable manner.

Summary

As described above, the operation device according to an aspect of the present invention is an operation device for remotely operating a target device. The operation device includes an operation unit that receives an operation from an operator, a determination unit that determines whether the operation received by the operation unit is a normal operation or an erroneous operation, and a control unit that transmits an operation signal corresponding to the operation received by the operation unit to the target device when the determination unit determines that the operation is a normal operation.

The operation device with this structure includes the determination unit, and transmits an operation signal when the determination unit determines that the operation is a normal operation, and does not transmit an operation signal for any erroneous operation performed on the operation unit. The operation device with this structure is prevented from causing an erroneous operation of its target device.

In the operation device according to the above aspect of the present invention, the determination unit may include a grip detection unit that detects whether the operation device is in a gripped state of being gripped by the operator. The determination unit may determine that the operation is a normal operation when the grip detection unit detects the gripped state.

The operation device with this structure transmits an operation signal only when being gripped by the operator. For an operation on the operation unit of the operation device that is not being gripped or for example is placed in a pocket, the determination unit determines that the operation is an erroneous operation. An operation signal is not transmitted in this case. This structure prevents the operation device from causing an erroneous operation of its target device.

In the operation device according to the above aspect of the present invention, the grip detection unit may include a plurality of sensors that detect a touch between the operation device and a human body. The grip detection unit may detect the gripped state when at least two of the plurality of sensors detect the touch.

The operation device with this structure does not transmit an operation signal corresponding to an operation performed on the operation unit to the target device only when at least two of the plurality of sensors detect a touch between the operation device and a human body. This structure more accurately prevents the operation device from causing an erroneous operation of its target device.

In the operation device according to the above aspect of the present invention, the plurality of sensors may detect the touch on a gripping part of the operation device that is to be gripped by the operator to operate the operation unit. The grip detection unit may detect the gripped state when the plurality of sensors detect a touch on the gripping part in two different directions.

The operation device with this structure can thus distinguish its state of being gripped by the operator and its state of being in contact with an object, such as a bed or a chair, and having its one side being pressed by the object.

In the operation device according to the above aspect of the present invention, the plurality of sensors may include a capacitance sensor, a pressure-sensitive sensor, or a mechanical switch.

The operation device according to the above aspect of the present invention may further include a recess that is sized in accordance with a size of a finger of the operator in the gripped state. The grip detection unit may include a sensor arranged in the recess, and the sensor may detect an object in the recess.

The operation device with this structure includes a recess that is sized in accordance with the size of a finger, and the determination unit detects whether the operation device is being gripped using the sensor arranged in the recess. Although the operation device placed in the operator's pocket may be in contact with a flat portion, such as a bed or a chair, the sensor for detecting the gripped state is arranged in the recess and thus the determination unit determines that the operation device is not in the gripped state. The recess sized in accordance with the size of a finger does not receive an object larger than a finger, and prevents the determination unit from erroneously detecting the gripped state.

In the operation device according to the above aspect of the present invention, the sensor may include a light emitter and a light receiver. The light emitter and the light receiver may face each other in the recess.

When the operator grips the operation device to place his or her finger in the recess, light emitted from the light emitter is blocked. This structure detects the operation device being gripped by the operator in a reliable manner.

The operation device according to the above aspect of the present invention may remotely operate the target device wirelessly.

The operation device with this structure can remotely operate the target device wirelessly.

An X-ray imaging unit according to another aspect of the present invention includes the operation device according to the above aspect, and an X-ray imaging device that is the target device.

The X-ray imaging unit with this structure includes the operation device that is prevented from causing an erroneous operation of its target device.

The embodiments disclosed herein should not be construed to be restrictive, but may be modified within the spirit and scope of the claimed invention. The technical features disclosed in different embodiments may be combined in other embodiments within the technical scope of the invention.

REFERENCE SIGNS LIST

1 X-ray imaging device (target device)
200 operation device
230 control unit
240 grip detection unit (determination unit)
241 front electrode (sensor)
242 rear electrode (sensor)
280 operation unit
300 X-ray imaging unit
400 operation device
401 recess
405 sensor
415 light emitter
420 light receiver

The invention claimed is:

1. An operation device for remotely operating a target device, the operation device comprising:
   an operation unit configured to receive an operation from an operator;
   a determination unit configured to determine whether the operation received by the operation unit is a normal operation or an erroneous operation;
   an acceleration sensor; and
   a control unit configured to transmit an operation signal corresponding to the operation received by the operation unit to the target device when the determination unit determines that the operation is a normal operation, wherein
   the determination unit includes an inclination detection unit configured to detect an inclination of the operation device based on an output value from the acceleration sensor and determine, based on the inclination, whether the operation received by the operation unit is a normal operation or an erroneous operation.

2. The operation device according to claim 1, wherein the operation device remotely operates the target device wirelessly.

3. An X-ray imaging unit, comprising:
   the operation device according to claim 1; and
   an X-ray imaging device that is the target device.

4. An operation device for remotely operating a target device, the operation device comprising:
   an operation unit configured to receive an operation from an operator;
   a determination unit configured to determine whether the operation received by the operation unit is a normal operation or an erroneous operation;
   a plurality of luminance sensors; and
   a control unit configured to transmit an operation signal corresponding to the operation received by the operation unit to the target device when the determination unit determines that the operation is a normal operation, wherein
   the determination unit including a luminance detection unit configured to determine, when all the plurality of luminance sensors are detecting light, that the operation received by the operation unit is a normal operation.

5. The operation device according to claim 4, wherein the operation device remotely operates the target device wirelessly.

6. An X-ray imaging unit, comprising:
   the operation device according to claim 4; and
   an X-ray imaging device that is the target device.

* * * * *